(12) United States Patent
Seguin

(10) Patent No.: US 10,639,154 B2
(45) Date of Patent: May 5, 2020

(54) INTERVALVULAR IMPLANT FOR A MITRAL VALVE

(71) Applicant: Jacques Seguin, Launen (CH)

(72) Inventor: Jacques Seguin, Launen (CH)

( * ) Notice: Subject to any disclaimer, the term of this patent is extended or adjusted under 35 U.S.C. 154(b) by 0 days.

(21) Appl. No.: 15/519,078

(22) PCT Filed: Oct. 12, 2015

(86) PCT No.: PCT/IB2015/057786
§ 371 (c)(1),
(2) Date: Apr. 13, 2017

(87) PCT Pub. No.: WO2016/059533
PCT Pub. Date: Apr. 21, 2016

(65) Prior Publication Data
US 2017/0224477 A1    Aug. 10, 2017

(30) Foreign Application Priority Data
Oct. 16, 2014    (FR) ..................................... 14 59917

(51) Int. Cl.
*A61F 2/24*    (2006.01)

(52) U.S. Cl.
CPC ...... *A61F 2/246* (2013.01); *A61F 2210/0014* (2013.01); *A61F 2220/0016* (2013.01); *A61F 2220/0075* (2013.01)

(58) Field of Classification Search
CPC ...... A61F 2/246; A61F 2/2442; A61F 2/2445; A61F 2/2448; A61F 2/2451; A61F 2/2454
See application file for complete search history.

(56) References Cited

U.S. PATENT DOCUMENTS

| 3,656,185 A | * | 4/1972 | Carpentier | ............ A61F 2/2448 |
| | | | | 623/2.36 |
| 4,490,859 A | | 1/1985 | Black et al. | |

(Continued)

FOREIGN PATENT DOCUMENTS

| WO | WO-2004/030568 A2 | 4/2004 |
| WO | WO-2004/030569 A2 | 4/2004 |

(Continued)

OTHER PUBLICATIONS

International Search Report & Written Opinion dated Nov. 19, 2015 in Int'l PCT Patent Appl. No. PCT/IB2015/057786.

(Continued)

*Primary Examiner* — Christopher D. Prone
(74) *Attorney, Agent, or Firm* — Eversheds Sutherland (US) LLP; Christopher C. Bolten; Nicola A. Pisano

(57) ABSTRACT

An intervalvular implant for a mitral valve having a frame and a membrane covering the frame is provided. The frame includes an elongated base portion formed by two curved or chevron branches connected to two connection areas of the implant for connecting to the annulus of the mitral valve. The frame further includes a longitudinal hoop extending in a plane substantially perpendicular to the plane in which the elongated base portion extends. The membrane is flexible and extends from one branch to the other branch while passing around the longitudinal hoop. The membrane may be connected to the branches without being stretched between the branches and the hoop so that the membrane forms lateral portions on each side of the implant that are able to transition between an outwardly convex, concave shape, and an outwardly concave, recessed shape.

14 Claims, 4 Drawing Sheets

(56) References Cited

U.S. PATENT DOCUMENTS

| | | | |
|---|---|---|---|
| 5,147,391 A | 9/1992 | Lane | |
| 5,213,575 A | 5/1993 | Scotti | |
| 5,376,114 A | 12/1994 | Jarvik | |
| 5,830,239 A | 11/1998 | Toomes | |
| 6,168,614 B1 | 1/2001 | Andersen et al. | |
| 6,269,819 B1 | 8/2001 | Oz et al. | |
| 6,461,382 B1 | 10/2002 | Cao | |
| 6,582,462 B1 | 6/2003 | Andersen et al. | |
| 6,613,086 B1 | 9/2003 | Moe et al. | |
| 6,911,043 B2 | 6/2005 | Myers et al. | |
| 7,037,333 B2 | 5/2006 | Myers et al. | |
| 7,077,862 B2 | 7/2006 | Vidlund et al. | |
| 7,399,315 B2 | 7/2008 | Iobbi | |
| 7,562,660 B2 | 7/2009 | Saadat | |
| 7,591,847 B2 | 9/2009 | Navia et al. | |
| 7,691,144 B2 | 4/2010 | Chang et al. | |
| 7,914,569 B2 | 3/2011 | Nguyen et al. | |
| 8,002,825 B2 | 8/2011 | Letac et al. | |
| 8,657,872 B2 | 2/2014 | Seguin | |
| 9,011,523 B2 | 4/2015 | Seguin | |
| 9,629,720 B2 | 4/2017 | Nguyen et al. | |
| 2005/0010287 A1 | 1/2005 | MacOviak et al. | |
| 2005/0137690 A1 | 6/2005 | Salahieh et al. | |
| 2005/0143689 A1 | 6/2005 | Ramsey, III | |
| 2005/0228495 A1* | 10/2005 | Macoviak | A61F 2/2412 |
| | | | 623/2.18 |
| 2005/0267573 A9 | 12/2005 | MacOviak et al. | |
| 2006/0058871 A1 | 3/2006 | Zakay et al. | |
| 2006/0195184 A1 | 8/2006 | Lane et al. | |
| 2007/0265701 A1 | 11/2007 | Gurskis et al. | |
| 2008/0033541 A1 | 2/2008 | Gelbart et al. | |
| 2008/0065204 A1 | 3/2008 | MacOviak et al. | |
| 2008/0125860 A1 | 5/2008 | Webler et al. | |
| 2008/0249618 A1 | 10/2008 | Huynh et al. | |
| 2009/0069890 A1 | 3/2009 | Suri et al. | |
| 2011/0022165 A1 | 1/2011 | Oba et al. | |
| 2011/0144742 A1 | 6/2011 | Madrid et al. | |
| 2011/0313434 A1 | 12/2011 | Kocaturk | |
| 2012/0215303 A1 | 8/2012 | Quadri et al. | |
| 2012/0271398 A1 | 10/2012 | Essinger et al. | |
| 2012/0323313 A1 | 12/2012 | Seguin | |
| 2013/0023985 A1 | 1/2013 | Khairkhahan et al. | |
| 2014/0350662 A1* | 11/2014 | Vaturi | A61F 2/2412 |
| | | | 623/2.1 |
| 2015/0039083 A1 | 2/2015 | Rafiee | |
| 2015/0119981 A1 | 4/2015 | Khairkhahan et al. | |

FOREIGN PATENT DOCUMENTS

| | | |
|---|---|---|
| WO | WO-2010/106438 A2 | 9/2010 |
| WO | WO-2013/178335 A1 | 12/2013 |

OTHER PUBLICATIONS

International Search Report and Written Opinion dated Aug. 8, 2016 in Int'l PCT Patent Application Serial No. PCT/IB2016/052498.

Textbook of Engineering Mathematics, Revised 2nd Edition, p. 76 (2005).

Written Opinion dated May 18, 2017 in Int'l PCT Patent Appl. Serial No. PCT/IB2016/052498.

* cited by examiner

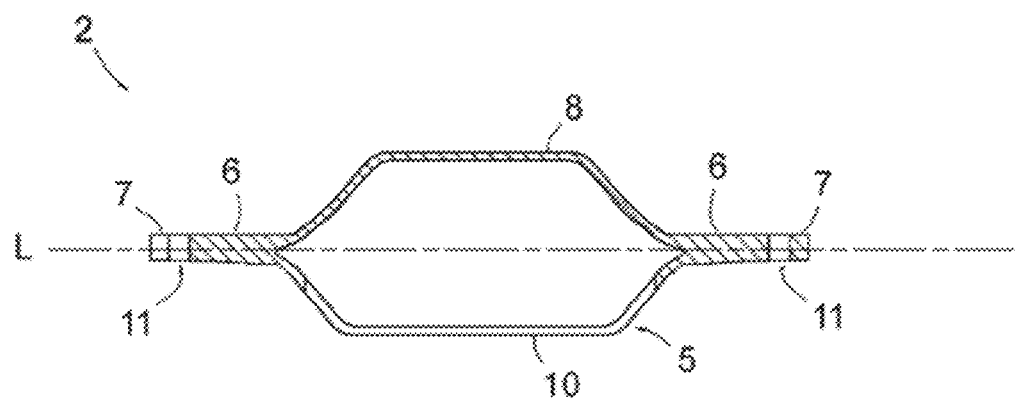
FIG. 1
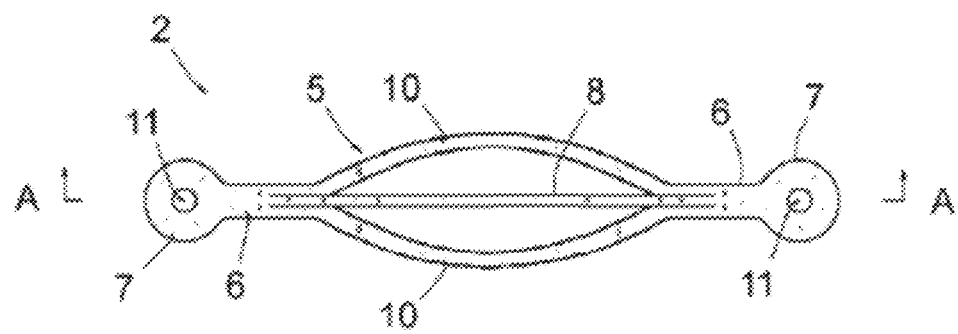
FIG. 2
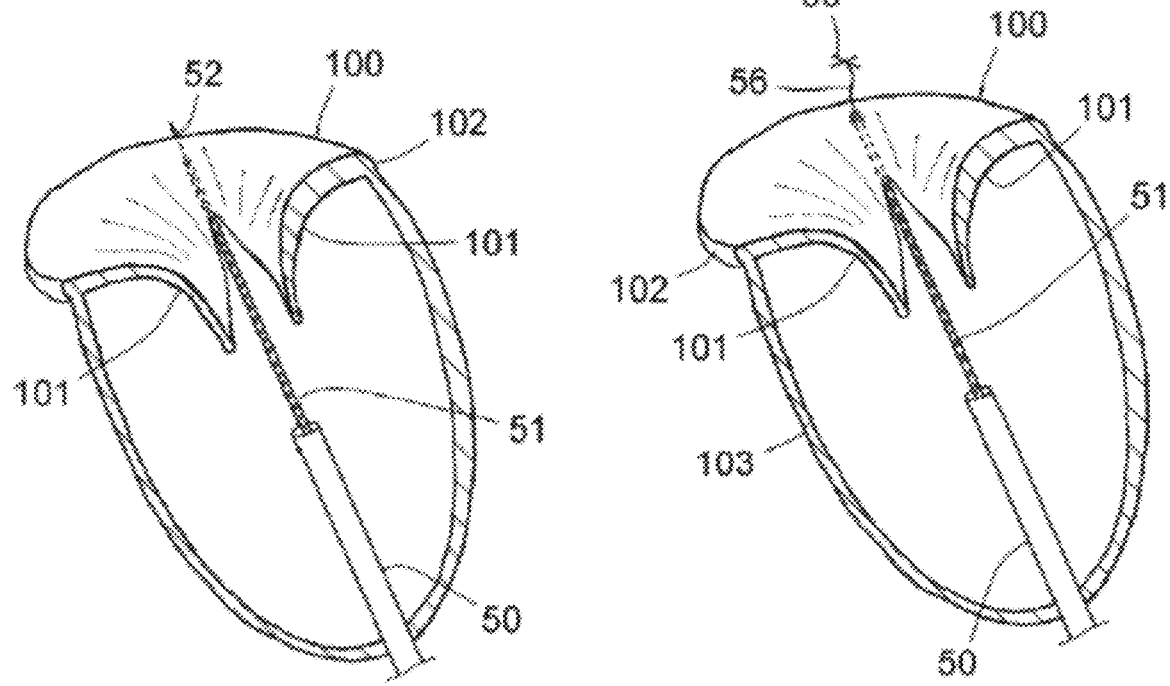
FIG. 3
FIG. 4

INTERVALVULAR IMPLANT FOR A MITRAL VALVE

CROSS-REFERENCE TO RELATED APPLICATIONS

This application is a national phase of International PCT Patent Application No. PCT/IB2015/057786, filed Oct. 12, 2015, which claims priority to French Patent Application No. 1459917, filed Oct. 16, 2014, the entire contents of each of which are incorporated herein by reference.

TECHNICAL FIELD

Background

The present invention relates to an intervalvular implant for a mitral valve.

The mitral valve of a heart, located between the left auricle and the left ventricle, may exhibit a loss of the seal of the two valvulae which it comprises, leading to regurgitation of the blood in the auricle during ventricular systole. This loss of seal frequently results from a loss of mobility of one of the two valvulae, following calcification of this valvula, distention of the mitral annulus, or infarction having led to damaging of the left ventricle.

It is known how to treat this problem by placing an implant between the valvulae, forming a supporting surface for the valvulae during the ventricular systole, and thereby allowing a seal to be given again to the mitral valve. An existing implant notably has a structure formed by a frame and by a membrane covering this frame.

However, known implants do not perfectly give satisfaction, either their shape is not optimum, causing imperfect restoration of the seal of the valve with respective to the blood flow from the ventricle to the auricle, or they do not operate properly and perturbed the blood flow from the auricle to the ventricle, or they have uncertain strength over time, or further they are difficult to implant.

The object of the present invention is to find a remedy to the whole of these drawbacks.

The patent application publication No US 2005/228495 A1 discloses a valve prosthesis comprising a frame base and a trestle that spans across and above the frame base, this trestle supporting a leaflet assembly comprising two mobile leaflet members that assume different complementing orientations in response to blood flow. The frame base is sized and configured to engage a generally circular shape of a native valve annulus. The outer edges of leaflet members are free of attachment to the frame base.

This device is intended to replace the native leaflets. It fails to achieve the object above-mentioned.

SUMMARY

The implant according to the invention has a structure formed with a frame and a membrane covering this frame; the frame has:
  an elongated base portion formed by two curved or chevron branches, these branches having median portions distant from each other and end portions getting closer to each other and being connected to connecting areas located at the longitudinal ends of the base portion; this elongated base portion has a width extending from the median portion of one branch to the median portion of the other branch and a length extending from one connecting area to the other connecting area, and is so elongated that said length is three to eight times greater than said width;
  anchoring portions connected to these connecting areas, allowing the implant to be anchored to the annulus of the mitral valve in two points of the annulus spaced from one another, in particular opposite one another;
  a longitudinal hoop extending from one connecting area to the other;
  the membrane is flexible and extends from one branch to the other while passing near the hoop, this membrane being connected to said branches without being stretched between these branches and this hoop so that the two lateral portions of the membrane thereby formed on both sides of the implant are able to adopt either a concave shape, outwardly convex, or a recessed shape, outwardly concave.

The implant, once it is set into place on a mitral valve, will occupy the intervalvular space, said membrane portions extending along the edges of the valvulae. By means of its frame only formed at this membrane by said branches and said hoop, this implant has a relative longitudinal flexibility allowing it to more or less adapt to the shape of the intervalvular space to be filled.

During a ventricular diastole, the pressurized blood from the auricle presses on the membrane portions and brings them into said recessed shape; the implant then has a shape relatively reduced in width, not interfering with the blood flow from the auricle to the ventricle. During a ventricular systole, the sac formed by the membrane on the ventricular side receives pressurized blood bringing said membrane portions into said convex shape; this shape allows the implants to perfectly fill the intervalvular space resulting from the faulty operation of one of the two valvulae and to form effective supporting surfaces for these valvulae, so assisting the latter.

According to a possible embodiment of the invention, the ends of the branches have tilted portions and/or the connecting areas are tilted or have tilted portions so as to shift said base portion on the ventricular side of the implant relatively to surfaces through which said anchoring portions are intended to come into contact with the annulus of the valve.

The implant according to this embodiment is intended to be set into place below a mitral valve, notably by a transapical approach, and said anchoring portions are intended to be connected to the annulus of the valve in two diametrically opposite points of this annulus. The aforementioned shift allows said membrane portions to in majority extend into the intervalvular space so that the free edges of the valvulae easily bear upon them.

It will be understood that the expression "ventricular side of the implant" refers to the side of the implant found on the side of the ventricle once this implant is set into place on a valve.

According to another possible embodiment of the invention, said connecting areas and said anchoring portions substantially extend in the extension of said base portion, so that this base portion is located in a plane close to the one in which extend the surfaces through which said anchoring portions are intended to come into contact with the annulus of the valve.

The implant according to this embodiment is intended to be set into place on the auricular side of the valve, through a transeptal approach, and said anchoring portions are intended to be connected to the annulus of the valve at the commissures of the valvulae. The free edges of the valvulae then however have more limited contact surfaces with said faces of the membrane.

Said branches may be positioned symmetrically relatively to a longitudinal median plane of the implant, so that said base portion has an oval or rhombic shape. The convex or protruding sides of said branches, resulting from said curved or chevron shape of these branches, may also be turned towards a same side of the implant, ensuring that said base portion has a general curved shape, substantially adapted to the curvature exhibited by the space delimited by the mitral valvulae (this curvature is often designated as a mitral "smile").

Said hoop is preferably located in the median longitudinal plane of the implant. It is also preferably located in a plane substantially perpendicular to the plane in which extends said base portion.

This anchoring portion may notably have a hole for receiving a tie for anchoring the implant to the mitral annulus. This hole may be oblong, notably with its length positioned perpendicularly to the length of the implant, in order to allow adjustment of the position of the implant relatively to the valve.

The membrane may extend on the whole of the portion of the implant along which extends the hoop, or on only part of this portion.

This membrane may possibly pass below the hoop and be connected to this hoop notably by a suture. However preferably, this membrane passes around the hoop by bearing against it.

Said branches and/or said hoop may have a circular or non-circular, notably square or rectangular, cross-section.

The frame may notably be in an elastically deformable material, allowing it to adopt a deformed configuration, with transverse contraction, in which it is able to be placed in a delivery catheter, and a normal expansion configuration, in which it is implanted. The elastically deformable material may notably be a shape memory material such as an aluminium and titanium alloy known under the usual name of Nitinol.

Said membrane may further be in a synthetic material, notably in a polyester fabric; it may also be in a natural material such as animal pericardium.

The connection of this membrane to the frame may be achieved by any suitable means, notably by a suture. The membrane, when it surrounds the hoop, may be only connected to said branches without being connected to the hoop; preferably it is connected both to said branches and this hoop.

BRIEF DESCRIPTION OF THE DRAWINGS

The invention will be well understood, and other features and advantages thereof will become apparent, with reference to the appended schematic drawing; this drawing represents as non-limiting examples, several possible embodiments of the implant concerned.

FIG. 1 is a side and longitudinal sectional view along the line A-A of FIG. 2, of a frame which this implant comprises, according to a first embodiment;

FIG. 2 is a top view thereof;

FIGS. 3 to 5 are very schematic sectional views of the ventricle and of the mitral valve of a heart, as well as of the instruments used, during the setting into place of the implant, during three successive steps for this setting into place;

DETAILED DESCRIPTION

Figure 8:
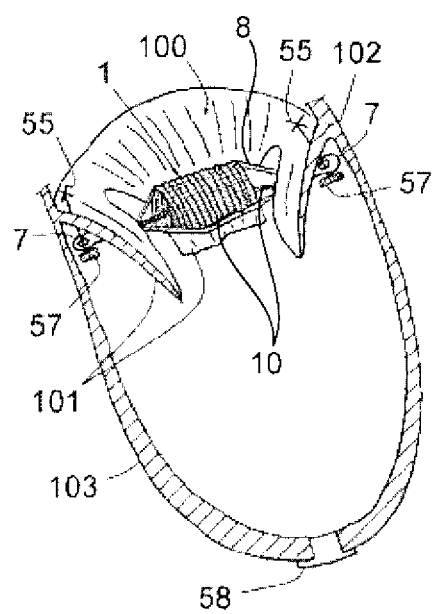
Figure 9:
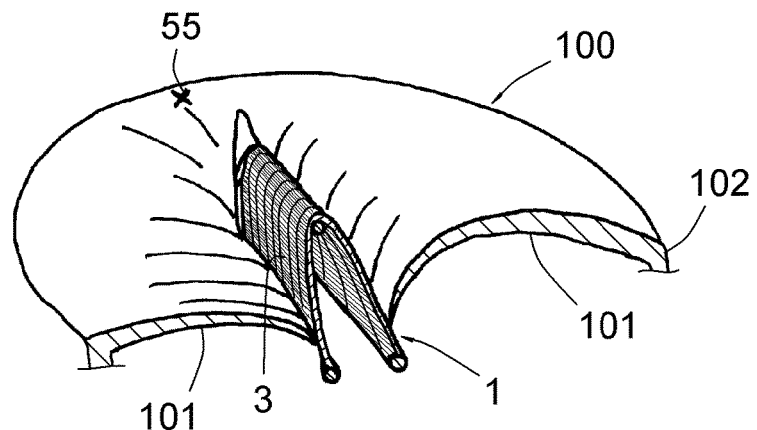
FIG. 9 is a perspective view of the mitral valve and of the implant set into place on this valve, with a cross-sectional view along the sectional plane of FIGS. 3 to 5.

FIGS. 8 and 9 illustrate an implant 1 according to the invention, set into place between the valvulae 101 of a mitral valve 100 in order to remedy a problem of loss of seal of these valvulae, which loss of seal leads to regurgitation of the blood into the auricle during the ventricular systole.

The implant 1 has a central portion extending between the valvulae 101 and two end portions allowing it to be anchored to the annulus 102 of the valve 100, and has a structure formed by a frame and by a membrane covering the central portion of this frame.

FIGS. 1 and 2 show the frame 2 of the implant 1 according to a first embodiment. This frame 2 has an elongated base portion 5, connecting areas 6, anchoring portions 7 and a hoop 8. It is in an aluminium and titanium alloy known under the usual name of Nitinol.

The base portion 5 is formed by two curved branches 10 positioned along general directions parallel to each other and symmetrically with respect to a longitudinal median plane of the implant 1. The median portions of these branches are located at a longer distance from each other than the end portions of these branches, so that said base portion 5 has a stretched oval shape. This base portion 5 extends in a plane substantially perpendicular to the longitudinal median plane of the implant 1.

The median portion of a branch 10 may be considered as extending over about the median third of the branch 10, and therefore each end portion may be considered as extending over about one third of the length of the branch 10.

These end portions become closer to each other towards the ends of the base portion 5 and join up with each other at their connection to the connecting areas 6. As visible in FIG. 1, they are bent at about half of their length so that the median portions of the branches 10 and the portions of these branches extending between the median portions and the bends formed by these branches 10, are shifted downwards relatively to a median height line L of the implant 1.

The connecting areas 6 substantially extend at this line L. They may slightly extend obliquely relatively to this line, like in the illustrated example, each area 6 having a height which increases from its end connected to the base portion 5 to its end connected to the anchoring portion 7.

Each anchoring portion 7 forms a surface intended to bear against the mitral annulus 102 and is pierced with a hole 11 intended to receive a tie 55 for anchoring to this annulus (see FIGS. 4 to 8).

The hoop 8 extends in the longitudinal median plane of the implant 1, from one connecting area 6 to the other, and above the line L. It has a median portion extending parallel to the median portions of the branches 10 and two lateral tilted portions connected to the areas 6. Said median portion of the hoop 8 represents about half of the length of this hoop (this length is considered to be in a straight line from one area 6 to the other).

The membrane 3 which the implant 1 also comprises is in a flexible material such as a polyester fabric or animal pericardium, and has a sealed structure towards the flow of the blood through it. As shown in FIGS. 8 to 11, it extends from one branch 10 to the other, passing around the hoop 8, without being stretched between these branches and this hoop. Thus, the two lateral portions 3a which it forms on both sides of the implant 1 are able to adopt either of the recessed shape, outwardly concave, visible in FIG. 10, or the rounded shape, outwardly convex visible in FIG. 11.

In the longitudinal plane, the membrane 3 essentially extends around the aforementioned median portion of the hoop 8 and the corresponding portions of the branches 10, as visible in FIG. 8.

In practice, as shown in FIG. 3, a catheter 50 is introduced into the left ventricle 103 through the apical area of this ventricle, and a catheter 51 of smaller diameter is engaged into this catheter 50 as far as below the mitral annulus 102. A rod 52 with a perforation tip is engaged through this catheter 51 and is used for perforating the mitral annulus 102 in two diametrically opposite locations of the valve 100.

After withdrawal of the rod 52, the catheter 51 is engaged through one of the perforations made and a tie 55 with deployable branches, connected to a thread 56, is then pushed into this catheter 51 as far as beyond the perforation, so that the branches of this tie are deployed beyond the annulus 102 (see FIG. 4). Traction on the thread 56 gives the possibility of bringing these branches of the tie 55 so that they bear against the annulus (see FIG. 5).

Figure 7:
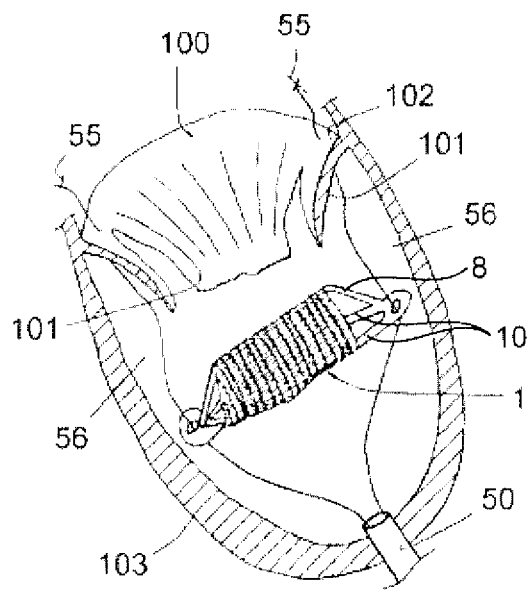
FIGS. 7 and 8 are similar views to FIGS. 3 to 5, taken along a sectional plane substantially perpendicular to that of FIGS. 3 to 5, during two subsequent steps of the setting into place of the implant.

A second tie 55 and a second thread 56, identical, are set into place in the same way in the second perforation (both of these ties 55 and threads 56 are visible in FIGS. 7 and 8).

Figure 5:
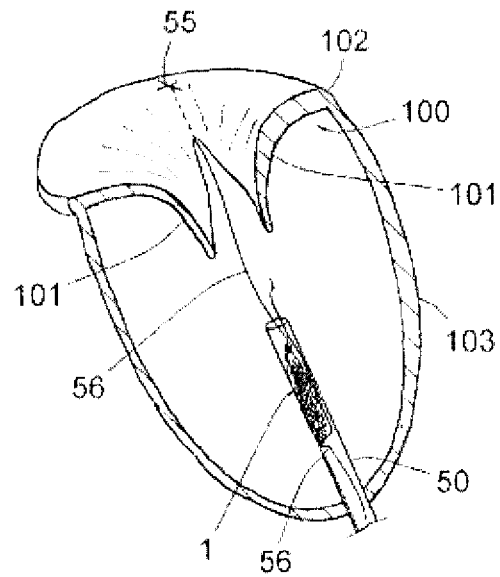
Figure 6:
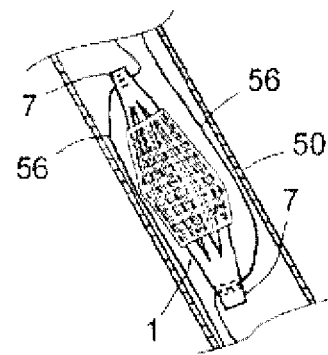
FIG. 6 is a sectional view of the instrument shown in FIG. 5, on an enlarged scale.

After withdrawal of the catheter 51, the implant 1 in the contracted state is pushed into the catheter 50 (see FIG. 5), with one of these anchoring portions 7 engaged on a thread 56 and the other anchoring portion 7 engaged on the other thread 56 as visible in FIG. 6.

The implant is then released from the catheter 50 (see FIG. 7) and is pushed on the threads 56 by means of catheters, until its central portion, i.e. the portion covered by the membrane 3, is engaged between the valvulae 101, as shown in FIG. 8, and that its anchoring portions 7 will come into contact with the mitral annulus 102.

Each anchoring portion 7 is then attached to the mitral annulus 102 by a known technique, notably by means of washers 57 able to slide on the threads 56 and be clip-fastened on the ties 55 (see FIG. 8).

The threads 56 are then cut by means of a rod with a sharp cutting edge, of a known type, slipped into the catheter 50.

As this appears in FIGS. 8 to 11, the implant 1, once it is set into place on the mitral valve 100, will occupy the intervalvular space and said portions 3a of the membrane 3 extending along the edges of the valvulae 101.

By means of its frame 2, only formed at this membrane 3, by the branches 10 and by the hoop 8, the implant 1 has a longitudinal relative flexibility allowing it to adapt to the shape of the intervalvular space to be filled. In this way, it is perfectly efficient for restoring the seal of the valve 100.

Figure 10:
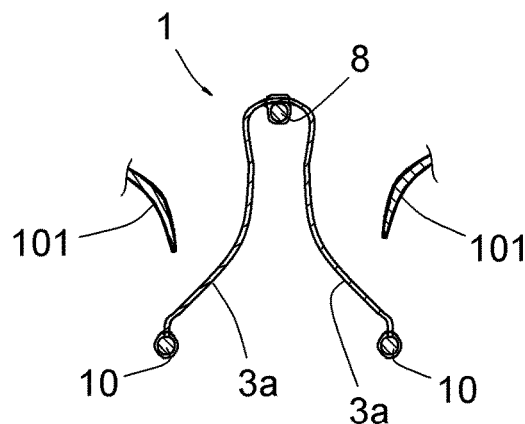
FIGS. 10 and 11 are sectional views of the valve and of the implant, respectively during auricular systole and during ventricular systole.
Figure 11:
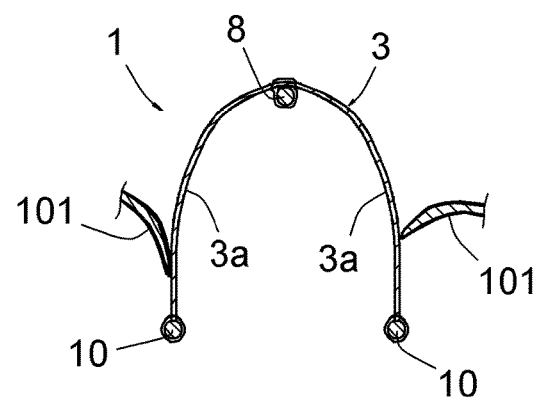

During ventricular diastole, the pressurized blood from the auricle (not shown in the figures) presses on the portions 3a of the membrane 3 and that brings them into the hollow outwardly concave shape, visible in FIG. 10; the implant 1 then has a shape relatively reduced in width, not interfering with the flow of the blood from the auricle to the ventricle. During ventricular systole, the sac formed by the membrane on the ventricular side receives pressurized blood, bringing said portions 3a of the membrane 3 into the convex shape visible in FIG. 11; this shape allows the implant 1 to perfectly fill the intervalvular space resulting from the faulty operation of one of the two valvulae 101 and to form efficient supporting surfaces for these valvulae.

At the end of the procedure for setting the implant 1 into place, a plug 58 is implanted on the ventricle 103 so as to close the apical orifice made for letting through the catheter 50, see FIG. 8.

Figure 12:
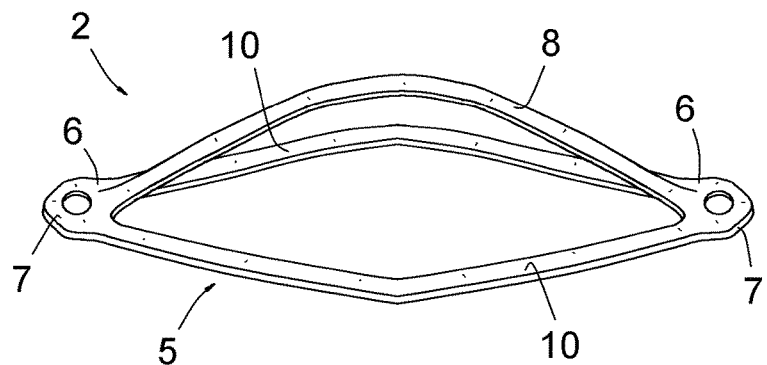
FIGS. 12 and 13 are views of the frame of the implant according to a second embodiment, in the deployed state, a perspective view and a top view respectively.
Figure 13:
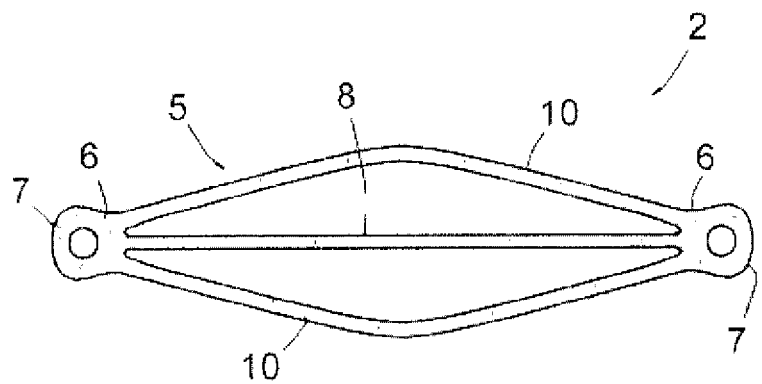

FIGS. 12 and 13 illustrate an implant 1 similar to the one described above but intended to be implanted on the auricular side of the valve 100, via a trans-septal approach. By simplification, the already described elements or parts, which are again found on this implant, are designated with the same numerical references.

On this frame 2, the connecting areas 6 and the anchoring portions 7 substantially extend in the extension of the base portion 5, so that the implant 1 is substantially planar outside the hoop 8. The anchoring portions 7 are then intended to be connected to the annulus 102 at the commissures of the valvulae 101.

Moreover, in the illustrated example, the branches 10 have a shape, not a stretched oval shape but a chevron shape, giving the base portion a rhombic shape. These branches 10 and the hoop 8 are further, also as example, with a rectangular cross-section.

Figure 14:
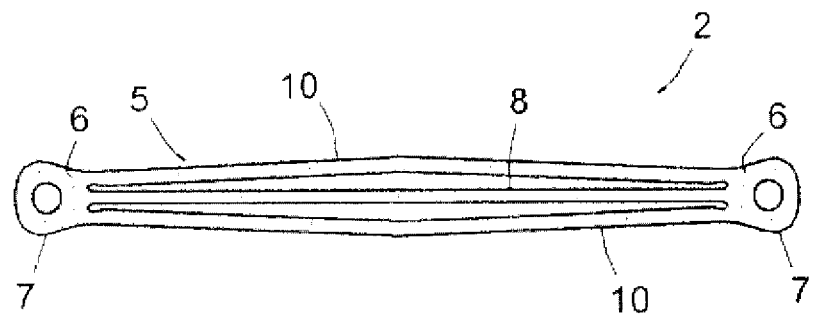
FIG. 14 is a top view of this frame, in the contracted state.

FIG. 14 shows the frame 2 in the longitudinal contraction state which it adopts when it is placed in the catheter 50.

Figure 15:
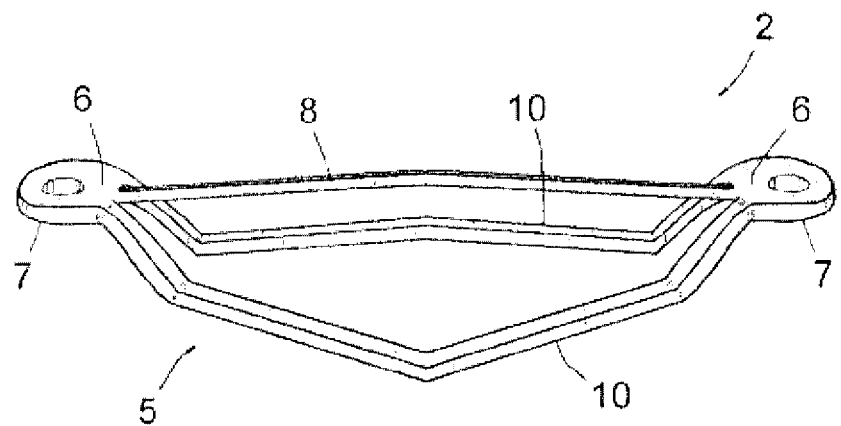
FIG. 15 is a view of the frame of the implant according to a third embodiment.

FIG. 15 shows a third possible embodiment of the frame 2, with also the use of the same numerical references for designating the already described elements or parts.

In this case, the base portion 5 is formed with chevron-shaped branches 10 therefore having a rhombic shape, and is shifted on the ventricular side of the implant 1, in the same way as described earlier. The hoop 8 has a small height as compared with the faces of the anchoring portions 7 intended to come into contact with the annulus 102 of the valve 100, so that the membrane 3 is located sufficiently low in the intervalvular space, and therefore closer to the area for setting the valvulae 101.

As this appears from the foregoing, the invention provides an intervalvular implant for a mitral valve having aforementioned determining advantages as compared with homologous implants of the prior art.

This invention has been described above with reference to embodiments provided as an example. It is obvious that it is not limited to these embodiments but that it extends to all embodiments covered by the appended claims.

The invention claimed is:

1. An intervalvular implant for a mitral valve, the implant comprising:
   a frame having an elongated base portion formed by first and second branches, each of the first and second branches having a curved or chevron shape, a first end portion, a median portion, and a second end portion, the median portions of the first and second branches spaced apart a width from each other, the first end portion of the first branch coupled to the first end portion of the second branch at a first connection area, the second end portion of the first branch coupled to the second end portion of the second branch at a second connection area, the first and second connection areas spaced apart a length from each other such that the length is three to eight times greater than the width between the median portions of the first and second branches, wherein the frame further comprises first and second anchoring portions connected to the first and second connection areas, respectively, the first and second anchoring portions configured to allow the implant to be anchored to an annulus of the mitral valve at two points of the annulus spaced apart and opposite each other, wherein the frame further comprises a longitudinal hoop extending from the first connection area to the second connection area; and a flexible membrane configured to extend from the first branch to the second branch while passing around the longitudinal hoop so that the flexible membrane forms a first lateral portion and a second lateral portion, the flexible membrane coupled to the first and second branches so that the first and second lateral portions of the flexible membrane are transitionable between a convex shape and a concave shape, wherein the flexible membrane is affixed to the first and second branches.

2. The implant of claim 1, wherein the first and second end portions of the first and second branches have tilted portions and/or the first and second connection areas are tilted or have tilted portions so as to shift the elongated base portion on a ventricular side of the implant relative to a surface of the annulus through which the first and second anchoring portions are intended to come into contact with the annulus.

3. The implant of claim 1, wherein the first and second connection areas and the first and second anchoring portions substantially extend in the direction of extension of the elongated base portion so that the elongated base portion is located in a plane close to a plane of the surface of the annulus through which the first and second anchoring portions are intended to come into contact with the annulus.

4. The implant of claim 1, wherein the first and second branches are positioned symmetrically relatively to a longitudinal median plane of the implant, so that the elongated base portion has an oval or rhombic shape.

5. The implant of claim 1, wherein convex or protruding sides of the first and second branches, resulting from the curved or chevron shape of the first and second branches, are turned towards a same side of the implant, ensuring that the elongated base portion has a general curved shape, substantially adapted to a curvature exhibited by a space delimited by the mitral valve.

6. The implant of claim 1, wherein the longitudinal hoop is located in a longitudinal median plane of the implant.

7. The implant of claim 1, wherein the longitudinal hoop is located in a plane substantially perpendicular to a plane in which the elongated base portion extends.

8. The implant of claim 1, wherein the first and second anchoring portions each have a hole configured to receive a tie for anchoring the implant to the annulus, the hole having a hole length positioned perpendicularly to the length of the implant between the first and second connection areas.

9. The implant of claim 1, wherein the flexible membrane extends along at least a portion of the implant over the longitudinal hoop.

10. The implant of claim 1, wherein the flexible membrane passes around the longitudinal hoop by bearing against the longitudinal hoop.

11. The implant of claim 1, wherein the flexible membrane is only coupled to the first and second branches without being coupled to the longitudinal hoop.

12. The implant of claim 1, wherein the flexible membrane is coupled both to the first and second branches and to the longitudinal hoop.

13. The implant of claim 1, wherein the frame comprises an elastically deformable material configured to allow the frame to adopt a deformed configuration, with transverse contraction, in which the frame may be placed in a delivery catheter, and a normal expansion configuration, in which the frame may be implanted.

14. The implant of claim 1, wherein the first and second anchoring portions are positioned on a longitudinal axis parallel to a longitudinal axis extending between the first and second connection areas.

* * * * *